United States Patent [19]

Givens

[11] Patent Number: 4,705,035

[45] Date of Patent: Nov. 10, 1987

[54] PARALLAX-FREE OPTICAL ZONE MARKER

[75] Inventor: Thomas B. Givens, Bradenton, Fla.

[73] Assignee: Visitec Company, Sarasota, Fla.

[21] Appl. No.: 902,766

[22] Filed: Sep. 2, 1986

[51] Int. Cl.$^4$ ............................................. A61F 9/00
[52] U.S. Cl. ............................... 128/303 R; 128/316; 33/670
[58] Field of Search ................. 128/303 R, 316, 304, 128/305; 604/112; 33/21.2, 27.01, 189, 191; 81/9.21; 30/302

[56] References Cited

U.S. PATENT DOCUMENTS

| | | | |
|---|---|---|---|
| 975,410 | 11/1910 | Fullmer et al. | 30/302 |
| 3,482,324 | 12/1969 | Samhat | 33/189 |
| 4,357,941 | 11/1982 | Golubkov et al. | 128/316 |
| 4,417,579 | 11/1983 | Soloviev et al. | 128/303 R |
| 4,520,815 | 6/1985 | Marinoff | 128/303 R |

Primary Examiner—Dalton L. Truluck
Assistant Examiner—F. Wilkens
Attorney, Agent, or Firm—Charles J. Prescott

[57] ABSTRACT

A parallax-free optical zone marker for use in radial karatotomy cornea surgery for impressing a temporary circular indentation into the cornea, the circular indentation to be used as a reference for radial incisions therefrom. The marker, integrally molded, includes an elongated handle and a collar portion disposed at one end of the handle. The lower end margin of the collar is preferrably circular an adapted to impress the circular indentation into the cornea with normal hand pressure applied through the handle. A passageway extends through the collar from its upper end margin to its lower end margin. Disposed within the passageway are a pair of crossplanes intersecting, preferably at ninety degrees one to another, along the longitudinal axis of the passageway, which axis intersects the center of the circular lower end margin. These crossplanes extend along substantially the entire length of the passageway but not to the lower end margin of the collar so as to prevent contact of the crossplanes with the cornea. The intersection of the crossplanes provides the user with viewable alignment means for assisting in the accurate orientation of the circular indentation. These crossplanes preferably taper in thickness toward their intersection for enhanced accuracy in the placement of the circular indentation. The marker is molded preferably of plastic in a wide range of sizes and may also be molded of clear or translucent material to increase light availability to the cornea as the circular indentation is made.

16 Claims, 6 Drawing Figures

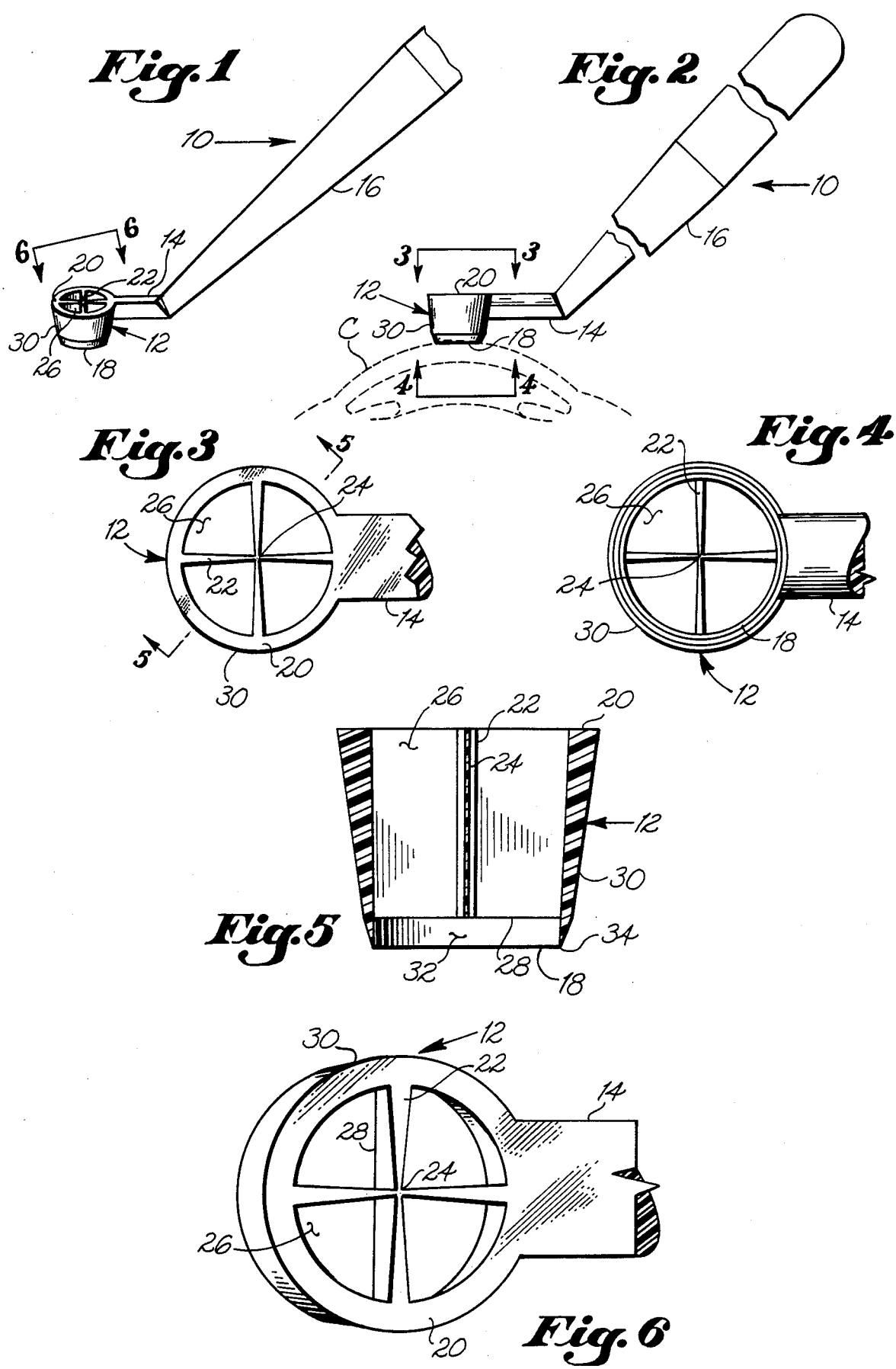

PARALLAX-FREE OPTICAL ZONE MARKER

BACKGROUND

This invention relates generally to radial keratotomy, and more particularly to optical zone markers in conjunction with such eye cornea surgical procedures.

Radial keratotomy is a relatively new surgical procedure for reducing myopia. Incisions are made in the cornea radially extending from the optical clear zone which tend to flatten the corneal surface, thereby reducing near sightedness and the cornea's optical power. Astigmatism may also be reduced in a similar procedure by placing the incisions in such a way that the cornea will flatten along one axis only. Although this procedure is widely practiced, long term effectiveness and safety have not been established.

Properly identifying and marking the opticl center of the visual axis of the patient's eye is a most important step in the preparation of the eye for surgery. If the optically clear zone to be later marked is only slightly decentered, the end of the radial incisions later made may encroach on the visual axis and increase the potential for problems of glare and astigmatism may also be induced. Prior to the marking of the center of the visual axis, the visual axis of the eye must be determined utilizing one of several well-known techniques. After the mark is accurately placed onto the patient's eye prior to surgery, an optical zone marker, properly sized to equal the diameter of the optically clear zone, is used by pressing it into the cornea, centered around the optical center mark, to cause a temporary circular indentation in the cornea to guide the placement of incisions.

To reiterate, radial keratotomy involves the making of incisions into the cornea radially extending from the optical center of the eye. However, these incisions do not extend to the optical center, but rather extend from a circle having its center at the optical center of the eye. The diameter of the circle from which the incisions radially extend varies depending on the scope of the corrective surgery required and the diameter of the patient's optical clear zone. Impinging on that optical clear zone by incision is one of the primary causes of post surgical glare problems.

Properly sized optical zone markers, then, are designed to be pressed onto the cornea around the optical center mark. These markers, which are primarily circular, but may also be oval, usually have a device such as a needle tip or cross hair to indicate the exact center of the circular marking edge for precise alignment on the cornea. The original tube-like optical zone markers in variously modified forms have been designed by Drs. Fyodorov, Hoffer, Berkeley and Thornton.

A primary problem with conventional optical zone markers results from binocular parallax as a result of the thickness of the outer tubular portion in relation to the cross hair or needle tip identifying its center. Again, serious degradation of the patient's eye may result if the optical zone mark imposed on the cornea is not accurately positioned in relation to the optical center of the eye.

An early technique for reducing this binocular parallax problem was achieved by reducing the length of the marker portion of optical zone markers, which have now been reduced down to about one millimeter long. Such markers are available from Storz, model number E-9030 in various diameters. It should be noted that this dimensional change only reduces, but does not eliminate, parallax error. Additionally, the cross hairs of some such devices have been known to inadvertently contact the cornea because the device was too short.

Nonetheless, because many optical zone markers continue to incorporate fine wire cross hairs to identify the center of the circular marker tube, the parallax problem remains as an element of inaccurate placing of the optical zone mark with such devices. These currently available instruments, having either cross hairs, needle point, or a centered ring within the generally circular marker tube to assist in aligning the instrument with the optical eye center and providing only one point in the vertical plane to be used in aligning the optical zone marker directly above the optical center, must be used extremely carefully while nonetheless running the risk of misalignment.

An additional problem associated with currently available optical zone markers resides in the user's requirement to have a wide range of sizes of such markers available from three millimeters to eight millimeters in diameter in one quarter millimeter increments. Because the currently available instruments are made of surgical stainless steel and are extremely expensive to manufacture, a complete set of such optical zone markers is extremely expensive.

Surgical stainless steel optical zone markers which include attached stainless steel cross hairs, include the inherent additional limitation that, after repeated use, the center sighting means may become loosened from the cylindrical tubular portion and have been known to fall into the patient's eye during surgery or be found inoperative when required.

A further problem resides in the fact that, as conventional optical zone markers are lowered close to the cornea's surface, the tubular portion of the marker, made of surgical steel, blocks out the available light striking the center portion of the cornea, thus reducing the visibility of the corneal surface. This further increases the difficulty of proper orientation prior to indenting the cornea.

The present invention provides features which overcome all of the above limitations. The parallax problem is virtually eliminated by the structure of the present invention; the cost of manufacturing a utilized injection molded part is insignificant and may be manufactured of various sizes inexpensively; the marker may be molded of clear material to reduce the light-obliterating limitation of surgical steel markers; manufacturing tolerances are at least as accurate, if not more so, than those found in conventional surgical stainless steel markers; the cross hairs, because integrally molded, virtually eliminate the possibility of these cross members falling into the patient's eye.

BRIEF SUMMARY OF THE INVENTION

This invention is directed to a parallax-free optical zone marker for use in radial keratotomy cornea surgery for impressing a temporary circular indentation into the cornea, the circular indentation to be used as a reference for radial incisions therefrom. The marker, integrally molded, includes an elongated handle and a collar portion disposed at one end of the handle. The lower end margin of the collar is preferably circular an adapted to impress the circular indentation into the cornea with normal hand pressure applied through the handle. A passageway extends through the collar from its upper end margin to its lower end margin. Disposed within the passageway are a pair of crossplanes intersecting, preferably at ninety degrees one to another, along the longitudinal axis of the passageway, which axis intersects the center of the circular lower end margin. These crossplanes extend along substantially the entire length of the passageway but not to the lower end margin of the collar so as to prevent contact of the crossplanes with the cornea. The intersection of the crossplanes provides the user with viewable alignment means for assiting in the accurate orientation of the circular indentation. These crossplanes preferably taper in thickness toward their intersection for enhanced accuracy in the placement of the circular indentation. The marker is molded preferably of plastic in a wide range of sizes and may also be molded of cler or translucent material to increase light availability to the cornea as the circular indentation is made.

It is therefore an object of this invention to provide an integrally molded optical zone marker which is virtually parallax free in use when locating a circular indentation for radial keratotomy surgery.

It is another object of this invention to provide an inexpensively molded optical zone marker in a wide variety of sizes.

It is another object of this invention to provide an optical zone marker which is single use.

It is another object of this invention to provide an integrally molded optical zone marker which virtually eliminates the possibility of the internal alignment means becoming detached either prior to or during surgery and falling into the patient's eye.

It is another object of this invention to provide an optical zone marker which permits light transmission into the collar and onto the cornea for more accurate placement of the circular indentation.

It is another object of this invention to provide an integrally molded optical zone marker which incorporates inherent manufacturing accuracy in the sizing, shaping and positioning of the lower end margin of the marker portion in relation to the viewable alignment crossplanes.

In accordance with these and other objects which will become apparent hereinafter, the instant invention will now be described with reference to the accompanying drawings in which:

BRIEF DESCRIPTION OF THE DRAWINGS

FIG. 1 is a perspective view of the marker portion and lower end of the handle disposed therefrom.

FIG. 2 is a side elevation view of the invention in relationship to the cornea of an eye shown in phantom.

FIG. 3 is a top plan view of the collar portion of the invention in the direction of arrows 3—3 in FIG. 2.

FIG. 4 is a bottom plan view of the collar portion of the invention in the direction of arrows 4—4 in FIG. 2.

FIG. 5 is a section view in the direction of arrows 5—5 in FIG. 3.

FIG. 6 is a view of the collar portion of the invention in the direction of arrows 6—6 in FIG. 1 to demonstrate the anti-parallax features of the invention.

DETAILED DESCRIPTION OF THE INVENTION

Referring now to the drawings, and particularly to FIGS. 1-5, the invention is shown generally at 10 and includes a handle 16 and a collar portion (or collar) 12 interconnected by lower handle portion 14. The preferred embodiment of the invention is integrally molded of plastic, wherein the collar portion 12 includes a tubular-shaped portion 30 within which is disposed a pair of crossplanes 22.

The crossplanes 22 are inwardly extending from the inner walls of tubular portion 30 to merge and interconnect along axis 24 which is centered within the cylindrical passageway 26 extending within the length of tubular portion 30. Tubular portion 30 has an upper end margin 20 and a lower end margin 18. As best seen in FIG. 5, the tubular portion 30 thickness tapers from its upper end margin 20 to its lower end margin 18 such that edge 34 is sufficiently sharp to impress into the cornea C a circular indentation when the marker 10 is pressed thereagainst by normal hand pressure via handle 16 as shown in FIG. 2.

This indentation impressed into the cornea C, as previously discussed, must be critically aligned to have its center coinciding with the visual axis of the eye. The user, having previously examined the eye, selects a particular size marker 10 which is provided in a variety of lower end margin 18 circular sizes. Prior to cornea C indentation, the user must aling the crossplane axis 24 with a preestablished marking representing the optical center of te eye. Enhanced by optical devices, nonetheless, the positioning of the lower end margin 18 is still accomplished visually by the sight aligning of axis 24 with the eye's optical center. To enhance the alignability of the invention, while maintaining strength of attachment of the crossplanes 22 to the inside of tubular portion 30, the thickness of the crossplanes 22 decreases toward the axis 24. Thus, the overall blocking effect of the crossplanes 22 is reduced substantially so as to increase the viewability of, and alignment with, the marking of the eye's optical center on the cornea C.

Because the cornea C has curvature, and because the only indentation desired in the cornea C is a circular indentation, the crossplanes terminate at the lower edge margin 28 slightly from the lower end margin 18 as best shown in FIG. 5. By this arrangement, then, a recess 32 is provided to insure that the lower edge margin 28 of the crossplanes 22 does not come in contact with the cornea C of the eye.

One of the important features of the present invention is in its ability to eliminate parallax error in aligning the circular lower end margin 18 with the optical center of the eye. Toward that end, the crossplanes 22 extend over substantially the entire length of the tubular portion 30, except for recess 32 as described hereinabove. Thus, the upper edge margins of the crossplanes 22 are in alignment with the upper end margin 20 of the tubular portion 30. To demonstrate the visual effect of parallax and the dramatic ease with which the user may detect such mislignment, FIG. 6 shows what the user would observe from a vantage point not in alignment with the axis 24 of the crossplanes 22. In such event, at least one of the lower edge margins 28 of the crossplanes 22 would be viewable such that the blocking effect from the axis 24 of the crossplanes 22 is substantially increased. Thus, to easily eliminate this misalignment due to parallax error, the user simply adjusts the viewing vantage point until no part of the sides and lower edge margins 28 of the crossplanes 22 is observed. In such instance, and when the axis 24 is coincident with the optical center of the eye, the invention is properly aligned for cornea C indentation in preparation for the upcoming surgery.

As the tubular portion 30 is positioned in proper alignment and contact with the cornea C, the tubular portion 30 has the effect of blocking out a substantial part of the surrounding incoming light striking the cornea C. To eliminate this light-blocking effect, the invention is preferrably injection molded of a clear plastic material. Alternately, the material may be translucent to have an ideal blend of light transmission and distinct viewable material in conjunction with the crossplanes 22 and axis 24 for alignment purposes.

To assist the surgeon in the accurate manipulation of the marker 10, handle 16 adjacent its distal end may include well-known surface texturing such as knurling (not shown) to enhance its gripability.

While the instant invention is shown and described herein in what is conceived to be the most practical and preferred embodiment, it is recognized that departures may be made therefrom within the scope of this invention, which is therefore not to be limited to the details disclosed herein, but is to be accorded the full scope of the claims so as to embrace any and all equivalent apparatus and articles.

What is claimed is:

1. An optical zone marker to be used in surgical ophthalmology for impressing into an eye cornea outer surface of a human eyeball a circular indentation whose imaginary center is substantially aligned with the eye's optical center, said marker comprising:
   an elongated handle and collar portion, said handle integrally molded with, and generally laterally extending from, said collar portion;
   said collar portion having a passageway therethrough having a central longitudinal axis and also having a pair of crossplanes diagonally disposed one to another across said passageway and extending longitudinally within said passageway;
   said collar portion having upper and lower end margins;
   said crossplanes having upper and lower edge margins and intersecting one another along said central axis;
   said collar portion lower end margin circular and having an imaginary center in alignment with said central axis and shaped to form the circular indentations into the eye cornea outer surface;
   said crossplanes lower edge margins recessed from said collar portion lower end margin sufficiently to provide clearance with respect to the eye cornea outer surface when said collar portion lower end margin is pressed against the eye cornea outer surface;
   said crossplanes intersection providing viewable alignment means for enabling a user, by grasping said handle, to visually align said central axis with the eye's optical center;
   said handle being laterally disposed so as to provide firm hand control and manipulation of said collar portion and a clear field of vision of said collar portion, the eye cornea, and the eye's optical center.

2. An optical zone marker as set forth in claim 1, wherein;
   said passageway is circular and axially aligned with said central axis.

3. An optical zone marker as set forth in claim 1, wherein:
   said crossplanes extend longitudinally to said collar portion upper end margin and are perpendicularly disposed one to another.

4. An optical zone marker as set forth in claim 3, wherein:
   said crossplanes narrow in thickness toward said central axis.

5. An optical zone marker as set forth in claim 2, wherein:
   said marker is molded of plastic.

6. An optical zone marker as set forth in claim 5, wherein:
   said plastic is translucent.

7. An optical zone marker as set forth in claim 5, wherein:
   said plastic is transparent.

8. An optical zone marker as set forth in claim 1, wherein:
   said handle is upwardly extending and includes a gripping surface for improved control of said marker.

9. An optical zone marker to be used in surgical ophthalmology impressing into an eye cornea outer surface of a human eyeball an oval indentation whose imaginary center is substantially aligned with the eye's optical center, said marker comprising:
   an elongated handle and collar portion, said handle integrally molded with, and generally laterally extending from, said collar portion;
   said collar portion having a passageway therethrough having a central longitudinal axis and also having a pair of crossplanes diagonally disposed one to another across said passageway and extending longitudinally within said passageway;
   said collar portion having upper and lower end margins;
   said cross planes having upper and lower edge margins and intersecting one another along said central axis;
   said collar portion lower end margin oval and having an imaginary center in alignment with said central axis and shaped to form the oval indentations into the eye cornea outer surface;
   said crossplanes lower edge margins recessed from said collar portion lower end margin sufficiently to provide clearance with respect to the eye cornea outer surface when said collar portion lower end margin is pressed against the eye cornea outer surface;
   said crossplanes intersection providing viewable alignment means for enabling a user, by grasping said handle, to visually align said central axis with the eye's optical center;
   said handle being laterally disposed so as to provide firm hand control and manipulation of said collar portion and a clear field of vision of said collar portion, the eye cornea, and the eye's optical center.

10. An optical zone marker as set forth in claim 9, wherein:
    said passageway is oval and axially aligned with said central axis.

11. An optical zone marker as set forth in claim 9, wherein:
    said crossplanes extend longitudinally to said collar portion upper end margin and are perpendicularly disposed one to another.

12. An optical zone marker as set forth in claim 11, wherein:
    said crossplanes narrow in thickness toward said central axis.

13. An optical zone marker as set forth in claim 10, wherein:

said marker is molded of plastic.

14. An optical zone marker as set forth in claim 13, wherein:

said plastic is translucent.

15. An optical zone marker as set forth in claim 13, wherein:

said plastic is transparent.

16. An optical zone marker as set forth in claim 9, wherein:

said handle is upwardly extending and includes a gripping surface for improved control of said marker.

* * * * *